(12) United States Patent
Radmer et al.

(10) Patent No.: US 8,579,861 B2
(45) Date of Patent: Nov. 12, 2013

(54) NEEDLE MAGAZINE

(75) Inventors: Bo Radmer, Hillerød (DK); Henrik Sønderskov Klint, Lyngby (DK); Johnny Kristensen, Roskilde (DK); Kristian Glejbøl, Glostrup (DK); Mikael Andersen, Malmö (SE); Lisbeth Kamstrup-Holm, Copenhagen (DK); Martin Von Bülow, Helsingør (DK); Peter Møller-Jensen, Hørsholm (DK); Philip Albert Sparholt, Smørum (DK); Thibaud Hofstätter, Helsingør (DK); Tue Kjærgaard Toft, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 641 days.

(21) Appl. No.: 12/670,091

(22) PCT Filed: Jul. 28, 2008

(86) PCT No.: PCT/EP2008/059896
§ 371 (c)(1),
(2), (4) Date: Sep. 16, 2010

(87) PCT Pub. No.: WO2009/016161
PCT Pub. Date: Feb. 5, 2009

(65) Prior Publication Data
US 2012/0016315 A1      Jan. 19, 2012

Related U.S. Application Data

(60) Provisional application No. 60/955,884, filed on Aug. 15, 2007.

(30) Foreign Application Priority Data

Jul. 28, 2007 (EP) .................................. 07113382

(51) Int. Cl.
*A61M 5/00* (2006.01)
*B65D 83/10* (2006.01)

(52) U.S. Cl.
USPC .......................................... 604/173; 206/366

(58) Field of Classification Search
USPC ........... 206/365–366; 604/181, 191, 206, 173
See application file for complete search history.

(56) References Cited

U.S. PATENT DOCUMENTS 4,836,373 A    6/1989  Goldman
4,848,569 A    7/1989  Leishman
(Continued)

FOREIGN PATENT DOCUMENTS

EP    0903155 A2    3/1999
EP    0903158 A2    3/1999
(Continued)

*Primary Examiner* — Kevin C Sirmons
*Assistant Examiner* — Bradley Osinski
(74) *Attorney, Agent, or Firm* — Wesley A. Nicolas; Marc A. Began; Reza Green

(57) ABSTRACT

A needle magazine for holding a plurality of injection needles (50) is described. The needle magazine comprises a first opening adapted to receive the device fluid access portion (120) of a medical delivery device. Each needle (50) is selectively moveable from a respective storage position not aligned with said first opening into a needle mounting position aligned with said first opening. The needle magazine further comprises needle positioning means (41). configured to alter the mutual position between a needle selected from said plurality of needles (50) relative to a neighbor needle when said selected needle moves from its storage position to the needle mounting position.

9 Claims, 10 Drawing Sheets

(56) References Cited

U.S. PATENT DOCUMENTS

Figure 1:
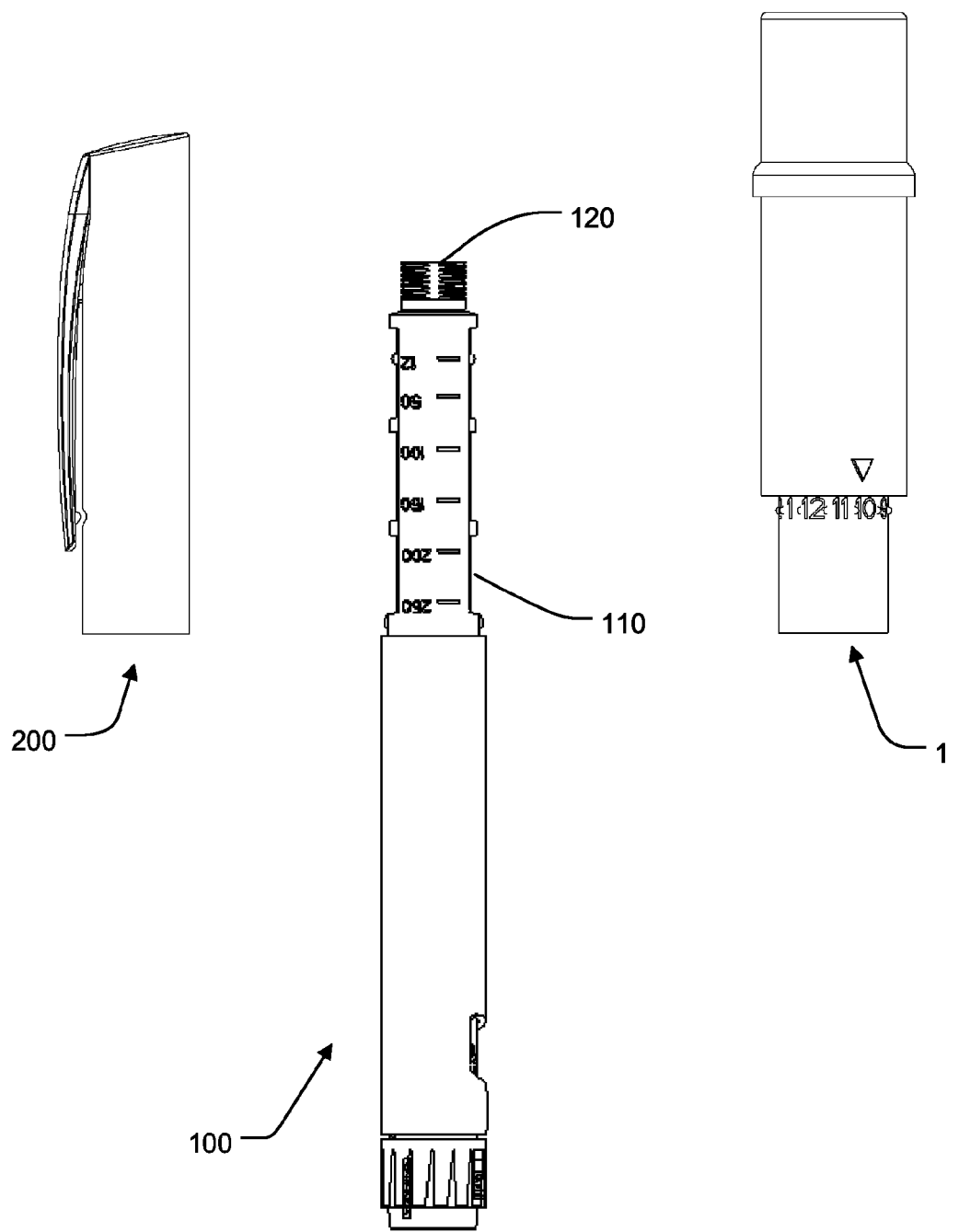

| | | |
|---|---|---|
| 5,224,596 A | 7/1993 | Kruger |
| 5,829,589 A | 11/1998 | Nguyen et al. |
| 5,873,462 A | 2/1999 | Nguyen et al. |
| 5,971,966 A | 10/1999 | Lav |
| 2002/0020646 A1 * | 2/2002 | Groth et al. .................. 206/366 |
| 2003/0014018 A1 | 1/2003 | Giambattista et al. |
| 2008/0312604 A1 | 12/2008 | Boesen |

FOREIGN PATENT DOCUMENTS

| | | |
|---|---|---|
| EP | 990446 A1 | 4/2000 |
| FR | 2623403 A1 | 5/1989 |
| FR | 2 671 730 A1 | 7/1992 |
| WO | 96/02290 A1 | 2/1996 |
| WO | 98/10812 A1 | 3/1998 |
| WO | 00/54691 A1 | 9/2000 |
| WO | 00/56379 A1 | 9/2000 |

* cited by examiner

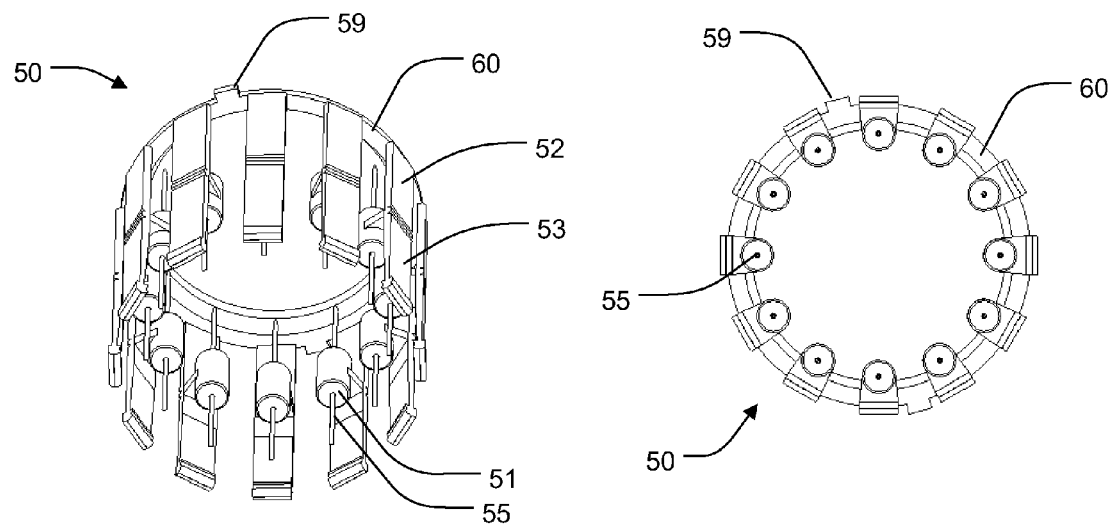
Fig. 3a
Fig. 3b
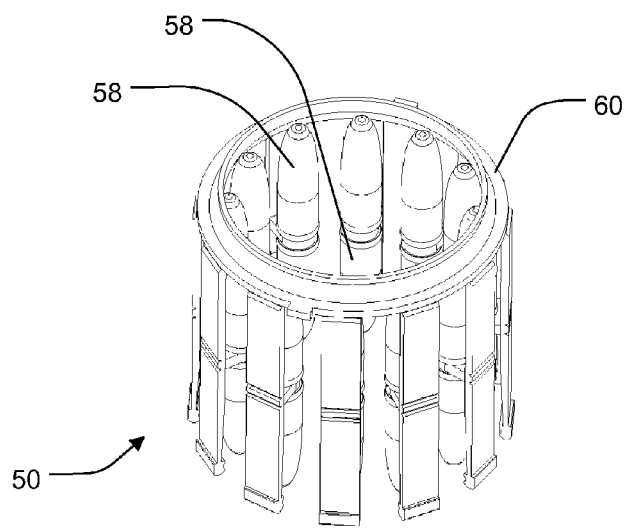
Fig. 3c

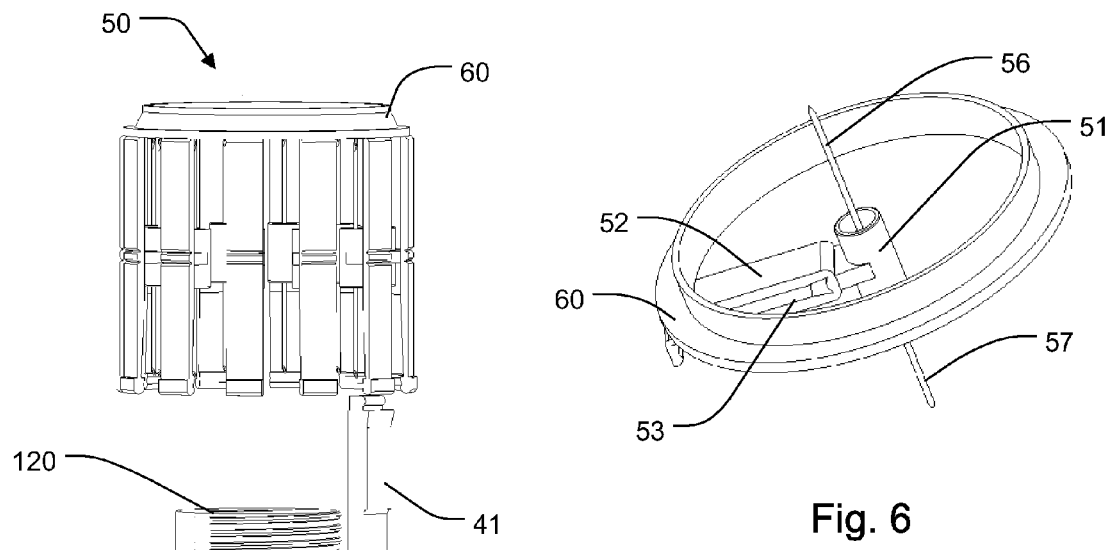
Fig. 4
Fig. 6
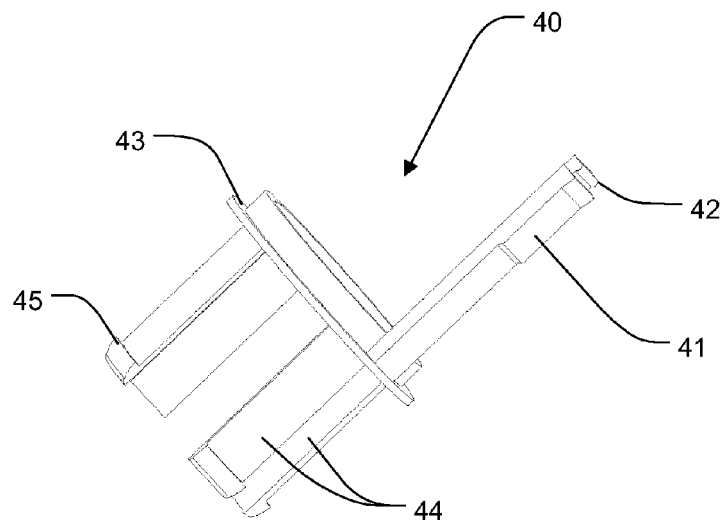
Fig. 5

US 8,579,861 B2

NEEDLE MAGAZINE

CROSS-REFERENCE TO RELATED APPLICATIONS

This application is a 35 U.S.C. §371 national stage application of International Patent Application PCT/EP2008/059896 (published as WO 2009/016161), filed Jul. 28, 2008, which claimed priority of European Patent Application 07113382.1, filed Jul. 28, 2007; this application further claims priority under 35 U.S.C. §119 of U.S. Provisional Application 60/955,884, filed Aug. 15, 2007.

FIELD OF THE INVENTION

The present invention relates to a needle magazine accommodating a plurality of injection needles for use with or incorporated into a medical delivery device. In particular the present invention relates to a needle magazine having means for positioning a selected needle from a storage position into a needle mounting position.

BACKGROUND OF THE INVENTION

Medical injection devices are used to deliver selected doses of medication to patients. Some medication, such as insulin is self-administered. The typical diabetes patient will require injections of insulin several times during the course of the day. In order to prevent infections it is recommended to use a sterile needle assembly for each injection. Needle assemblies are often delivered in magazines where each magazine contains only one needle assembly in a sterile compartment. Such a magazine is described in U.S. Pat. No. 5,971,966. Using a needle assembly of this kind requires the patient to open the magazine and to fasten the needle assembly on to the injection device prior to each injection. The storage of sterile needle assemblies of this type and the final disposal of used needle assemblies present a problem since new sterile needle assemblies are often carried loosely in purses or briefcases. Furthermore, used needle assemblies are often disposed of unsafely.

To overcome these problems a needle magazine for storing and dispensing a plurality of needle assemblies has been proposed in U.S. Pat. No. 5,829,589. The needle magazine is provided as a container having a plurality of cavities each accommodating a needle assembly. A cover is rotatably mounted on top of the container. When aligning a slot in the cover with one of the cavities, the user can access the cavity. The needle assembly is connected to the injection device by forcing the tip of the injection device into the cavity where the needle assembly is force fitted, e.g. by a well-known luer-coupling, onto the tip of the injection device. The needle assembly can then be detached from the magazine. When the used needle is to be returned to the magazine the user has to conduct a reverse procedure.

The above prior art needle magazine is attached to the injection device by fitting the entire magazine into an open end of the removable cap of a pencil-shaped injection device. Due to the dimensions of a pencil-shaped injection device only five needle assemblies can be contained in the magazine. An ordinary disposable injection device usually contains 300 IU of insulin. For many diabetes patients this is sufficient for 10 to 20 injections, therefore one magazine of needle assemblies are not enough for the lifetime of one disposable injection device, which is very inconvenient.

US 2002/0020646 discloses another needle magazine which is intended to be mounted onto the dispensing portion (the distal end) of an injection device. The needle magazine includes a rotatable cassette holding a plurality of needles in a circular array configuration. By sequentially rotating the cassette, each of the needles can be brought into alignment with the distal end of the injection device. By moving the injection device in the distal direction, the back needle of the particular selected needle penetrates a septum in the cartridge. Further distal movement causes the front needle to penetrate a seal in a distal face of the needle container to bring the selected needle into an injection position.

Even though the needle magazine according to US 2002/0020646 may include a large number of needles, this needle magazine is rather bulky and takes up much space in the plane which includes the array. If the needle magazine is dimensioned to hold several needles, the circular array extends quite far in a direction transverse to the needle which is aligned with the cartridge, particular in the direction which intersects the centre axis of the circular array. Thus, the geometric form of the needle magazine according to US 2002/0020646 is practically not adaptable to all kinds of injection devices, in particular not to injection devices of the pen-shaped form factor.

BRIEF DESCRIPTION OF THE INVENTION

Having regard to the above-identified prior art devices, it is an object of the present invention to provide a needle magazine which is more easily adaptable to various differently shaped medical delivery devices and wherein the needle magazine holds a plurality of injection needles in a space efficient manner.

In a first aspect the present invention relates to a needle magazine for use with a medical delivery device, such as an injection device, the delivery device having a needle mounting portion including a device fluid access portion which, when the medical delivery device is coupled to the needle magazine, defines a needle mounting space extending in a direction distal to the device fluid access portion. The device fluid access portion may be provided with a piercable septum to which the needles of the needle magazine connects. The needles may be moved partly or completely into the needle mounting space to occupy a needle mounting position whereafter by subsequent movement, the needle may be coupled to the device fluid access portion for establishing fluid communication with the delivery device. The delivery device accommodates a medicament filled reservoir, such as a cartridge, which holds the device fluid access portion. The needle magazine comprises a needle support structure adapted to couple to or receive a needle mounting portion of the medical delivery device. The needle magazine further comprises a plurality of injection needles supported by the needle support structure and positioned in respective storage positions, whereby the needles form a needle cluster. Each needle is selectively moveable from their respective storage position arranged outside the needle mounting space and into a needle mounting position where a selected needle is moved partly or completely into the needle mounting space. The needle magazine further comprises needle positioning means configured to alter the relative position between a needle selected from said plurality of needles relative to a neighbour needle when said selected needle moves from its storage position and into the needle mounting position.

In some embodiments, the needle mounting space is defined as a cylindrical volume or alternatively as a frusto-conical volume.

Each of the needles of the needle cluster may comprise a first pointed end adapted to penetrate the skin of a user, i.e. forming a front needle, and may also comprise a pointed opposite end adapted to penetrate a container septum, i.e. forming a back needle. In some embodiments the front needle and the back needle extends along a common axis. In other embodiments the axis of the front needle is different than the axis of the back needle. In still other embodiments, instead of a back needle, each of the needles comprises connecting means such as a luer connection for connecting with the medicament reservoir of the medical delivery device. The needle may define a needle mounting axis along which the needle is adapted to couple to the device fluid access portion of the medicament reservoir for establishing fluid communication.

When the needles of the cluster are stored in their respective storage positions, the needles may form an array having regularly or irregularly distributed needles, i.e. the needles do not necessarily need to be arranged in an evenly spaced configuration.

When a selected needle is positioned in the needle mounting position, the needle may be moved in a direction substantially parallel with the needle mounting axis towards the device fluid access portion of the medical delivery device. When a needle is positioned in the needle storage position, the particular needle is not facing the device fluid access portion. However, when the needle is positioned in the needle mounting position, the needle is facing the device fluid access portion.

When the device fluid access portion is provided as a septum which may comprise either a flat or curved surface, the needle mounting axis may either be arranged for intersecting the front surface of the septum at a right angle or intersecting the septum at angles differing from 90 degrees.

By moving the selected needle relative to one or more of the remaining needles in the needle cluster upon moving the selected needle from its position outside the needle mounting space and into the needle mounting space, a solution is provided which allows the cluster to be arranged relative to the needle mounting portion of the device with greater design freedom, which thus facilitates a more space efficient design.

In a further aspect of the invention the plurality of needles when positioned in their storage position forms an array where the mutual spacing between a first needle and a neighbouring needle is defined by a first distance, and wherein needle positioning means moves a selected one of said needles from its storage position to the needle mounting position so that the mutual distance between the needle in the needle mounting position to a neighbour needle is larger than said first distance.

In such a configuration, a densely arranged needle array configuration may be used where a selected needle is separated from other needles of the array upon moving the selected needle into the needle mounting space. By such provisions it is ensured that the needles in their storage position are closely packed to form a compact needle magazine. However, at the time of mounting a new needle, by separating the selected needle from other needles of the remaining array, it is ensured that the coupling of the needle mounting portion of the medical delivery device with the selected needle takes place without interfering with neighbouring needles. Thus, a large number of needles may be stored in a very space efficient manner.

In some embodiments, the plurality of needles, when stored in their storage positions, are arranged in a ring shaped array configuration. The ring shaped array may be provided as a cylindrical array configuration where the needles are arranged with parallel axes. Alternatively, the circular array is defined as a cone array configuration where the axes of the needles intersects at a point along a distal or proximal direction. In further embodiments, the particular needles may be angled differently with respect to a first axis of the array, so that some of the needles may be arranged parallel with the first axis while other needles of the array may be arranged for intersecting the first axis. In still further embodiments, the needle magazine may be so designed as to vary the angle between a selected needle with respect to the first axis in the course of operating the needle magazine, i.e. when a particular needle is moved about in the interior of the needle magazine.

When the needle array is formed so as to define a central axis, said device fluid access portion of the delivery device may be arranged along the central axis of the needle array. Such configuration is particularly effective in applications where the outer shape of the needle magazine should adapt to a pen-formed injection device, which is adapted for use with cylindrical cartridges having a central longitudinal axis.

Each needle of the needle magazine may be mounted in a respective needle hub connected to a pivot support structure. The pivot support structure may be configured to move the needle hub from the storage position into the needle mounting position responsive to actuation of the position means. When pivoting, the needle hub may be moved along an arcuate path into alignment with the needle mounting portion. During this movement, the axis of the needle (e.g. the axis of the back needle) may be kept parallel with the axis of the needle in the aligned position, i.e. the axis of the needle in the mounting position. Alternatively, the orientation of the needle is altered during the pivotal movement. Subsequent movement of the needle to establish fluid communication with the medicament reservoir may be facilitated by a substantially translatoric movement of the selected needle, e.g. so as to pierce the septum of the container of the device.

The needle magazine may include an actuator member adapted to selectively engage at least one of the pivot support structures, the actuator member being moveably arranged with respect to the pivot support structure to actuate said pivoting movement. Alternatively, a plurality of actuator members are provided, such that each of the pivot support structures is adapted to be engaged by an actuator member dedicated that particular pivot support structure.

The needle support structure may define a housing of the needle magazine and may comprise at least one cap member which is slideably arranged with respect to the medical delivery device when the needle magazine is coupled thereto. The needle positioning means may be so configured that when the at least one cap member slides with respect to the delivery device, or alternatively, with respect to a second member of the needle magazine, the actuator member actuates the positioning movement and thus said pivoting movement.

Alternatively, or in addition, the sliding movement of the at least one cap member causes a front needle portion of a needle positioned in the needle mounting position to protrude through a needle passage formed in said at least one cap member. Such a configuration is useful when a needle shielding mechanism, where the needle(s) is/are hidden during injection, is required. Alternatively, or in addition, said sliding movement causes a back needle portion of a needle positioned in the needle mounting position to penetrate a septum part of a container mounted in the medical delivery device.

In some embodiments, the needle magazine as defined above comprises a rotatable index mechanism for sequentially rotating and aligning the plurality of needles with respect to the actuator member.

In further embodiments, the index mechanism is configured to operate in discrete steps. The index mechanism may comprise means for axially blocking the sliding movement of the at least one cap member at one or more pre-defined rotatable position(s) of the index mechanism. In some embodiments, every second step defines consecutive selectable needles of the needle array. In each of the intermediary steps, the slideable movement is blocked by the blocking means.

The index mechanism may be provided with a one-way mechanism, such as a ratchet mechanism. This ensures that the index mechanism cannot be reversed to select a previously used needle. Also, the index mechanism may be provided with a 360 degrees lock which ensures that needles that have once been used cannot be reselected.

In a further embodiment each of the plurality of needles of the array is mounted in a respective needle hub which is arranged to slide along a segmented track. The track has a first segment wherein a plurality of the needles may be stored in their storage positions so that they form said needle array, e.g. a linear array, where the needles are arranged outside the needle mounting space when the medical delivery device is coupled to the needle magazine. A second segment of the track is arranged so that a selected needle can be moved from the first track segment to the second track segment into a needle mounting position inside the needle mounting space when the medical delivery device is coupled to the needle magazine. Hereafter, the selected needle may be coupled to the device fluid access portion to establish fluid communication with the medicament reservoir.

A further third track segment may be provided to move used needles to the third track segment.

Some embodiments further include an actuator member which is adapted to sequentially engage a respective needle hub for moving a selected needle from its storage position in the first track segment into the needle mounting position in the second track segment and optionally further on to the third track segment.

In a further aspect of the invention, the invention relates to a needle magazine for use with a medical delivery device, the medical delivery device having a medicament reservoir and a device needle mounting portion, the needle magazine comprising: a): a needle support structure adapted to attach to the medical delivery device, and b): a plurality of injection needles supported by the needle support structure and forming a needle cluster, each needle having a longitudinal part which extends towards a pointed end of the needle. Each needle is selectively moveable from a respective storage position towards a needle mounting position where it is positioned adjacent said device needle mounting portion to allow subsequent positioning to establish fluid communication with the medicament reservoir.

Each of the needles may define a respective needle storage axis. When a selected needle is moved from the needle storage position into the needle mounting position, at least a part of the selected needle is moved in a direction away from its respective needle storage axis, i.e. it moves relatively to one or more of the remaining needles. The movement may be purely translatory or may follow an arcuate path. Hence, in such embodiments, the needle magazine further comprises needle positioning means configured to move a selected needle at least partly sideways relative to a respective neighboring needle upon at least a part of its movement towards the needle mounting portion.

Each of the embodiments described may employ a sterile barrier enclosing each needle. In some embodiments, the sterile barrier is formed as a piercable cap connected to the front needle part of the needles. Also for embodiments involving back needle parts, similar piercable caps may be provided for protecting the back needle parts.

In some embodiments, the needle magazine is adapted to removably attach to the medical delivery device. Such removable attachment may be provided as a snap connection to the cartridge holding part of the device, or alternatively, to the dosing assembly of the device. Still, in another alternative form, the needle magazine connects directly to a container of the device. In still other embodiments, the needle magazine does not attach to the medical delivery device but rather is adapted to align the two devices during mounting/demounting of the needle. In such embodiments, a selected needle may be connected to the medical delivery device so as to be separated from the remainder of the needle magazine during drug administration.

In a still further embodiment, the needle magazine attaches non-removably to the medical delivery device so as to form one unitary disposable assembly. Alternatively, the needle magazine is provided as a unitary device holding a medicament container, the unitary device being coupleable to a dosing assembly, thus, when coupled to the dosing assembly, forming a complete medical delivery system.

In any of the embodiments mentioned, the plurality of needles may be connected by a support structure so that the array forms a needle hub assembly whereby the needle hub assembly may be removed from the needle magazine when it has been used for replacement with a new needle hub assembly. In case the needle magazine forms part of a unitary medical delivery device/needle magazine, such a needle hub assembly may likewise be mounted removeable.

It is to be noted, that within the context of the present invention, when a selected needle is aligned with the needle mounting portion of the delivery device, the needle is not necessarily positioned exactly along an axis defined by a central axis of a rotational symmetric container. Rather, in this context, "aligned" means that an axis defined by the back needle, when the needle is aligned with the needle mounting portion, intersects the container septum at a location where the septum is penetrable by the back needle.

In the context of the present invention, the term "medical delivery device" shall be understood as any device capable of administering a medicament-containing flowable drug through a cannula. Examples of medical delivery systems are infusion pump applications, dosers, pen-shaped injectors, motor-dosers, and automated syringes such as the AutoPen™.

It should be noted that in addition to the needles forming the array as defined in the appended claims, the needle magazine may be provided with additional needles such as a needle intended for use before the needles forming the needle array. Such additional needle is not necessarily required to move in the same way as the remaining needles, as the first needle may be positioned in the mounting position already at the time of manufacture.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 2:
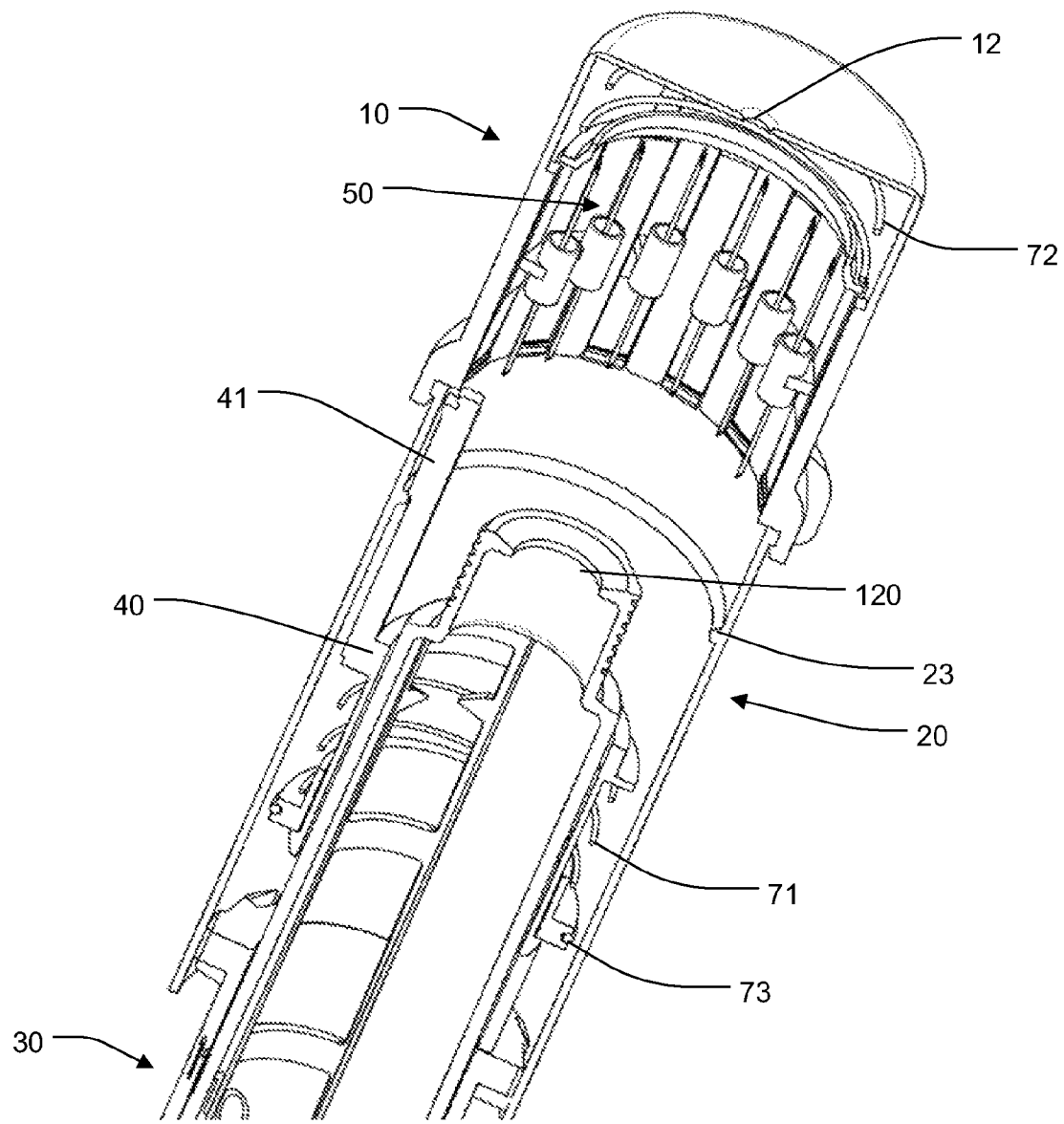
Figure 7:
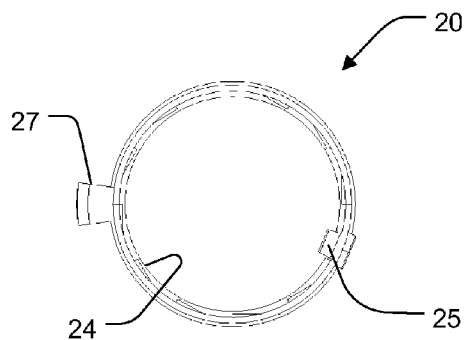
Figure 8:
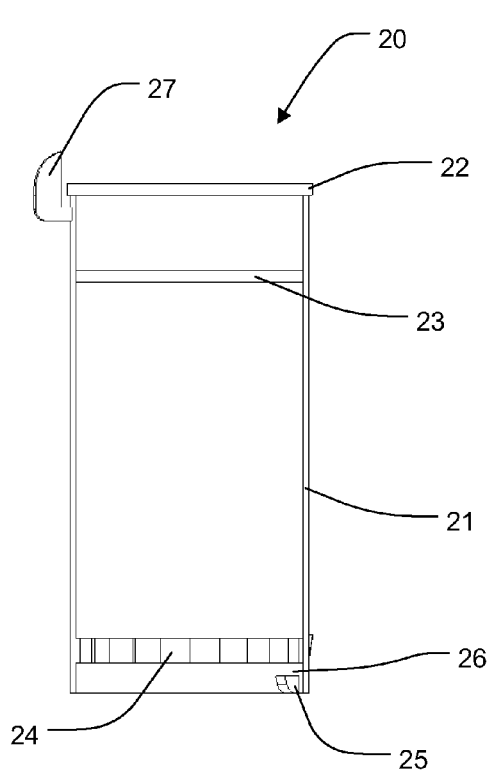
Figure 9:
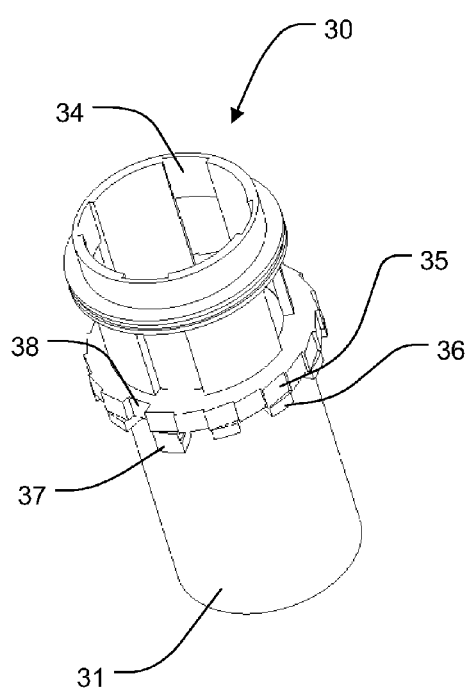
Figure 10:
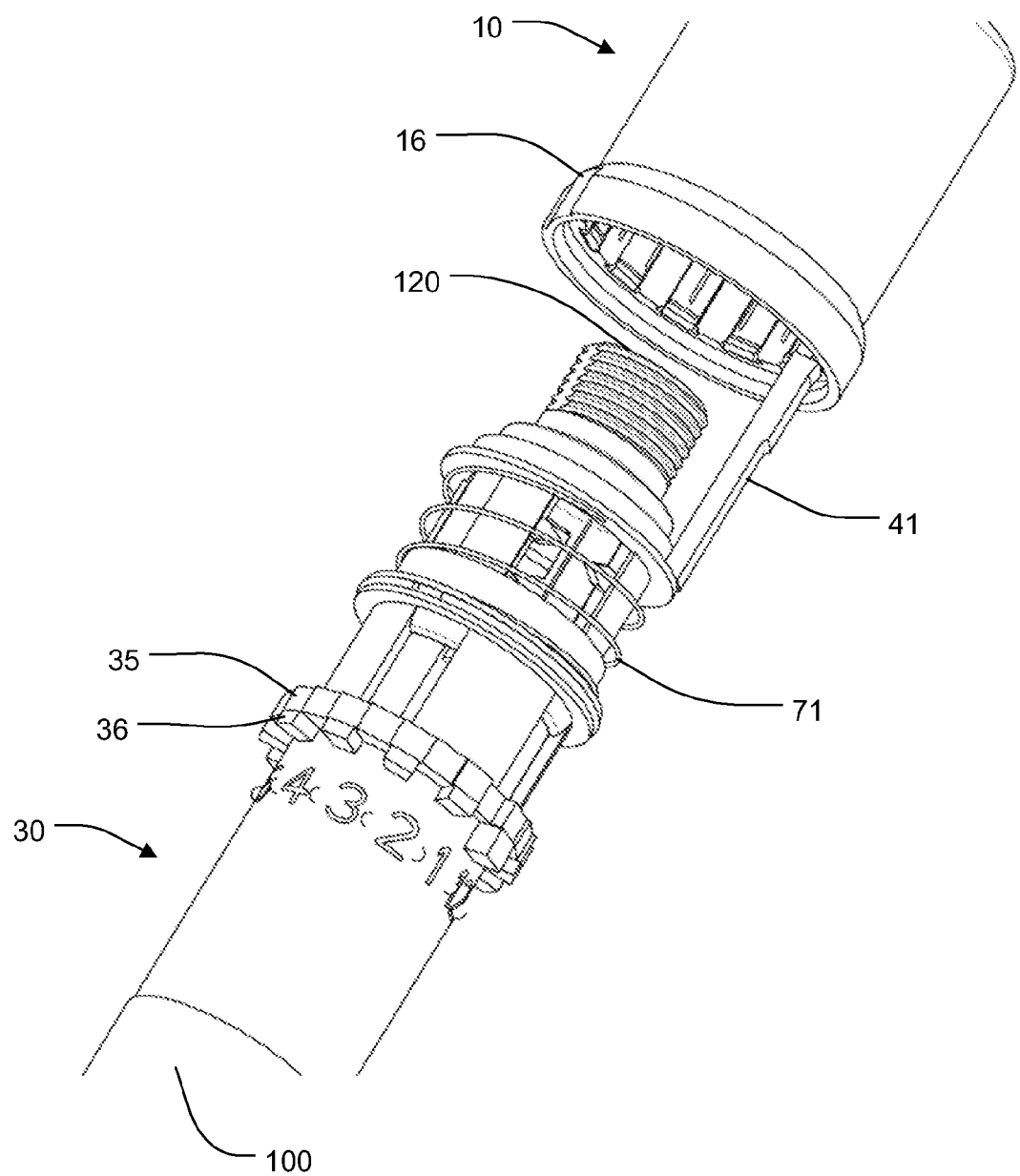
Figure 11A:
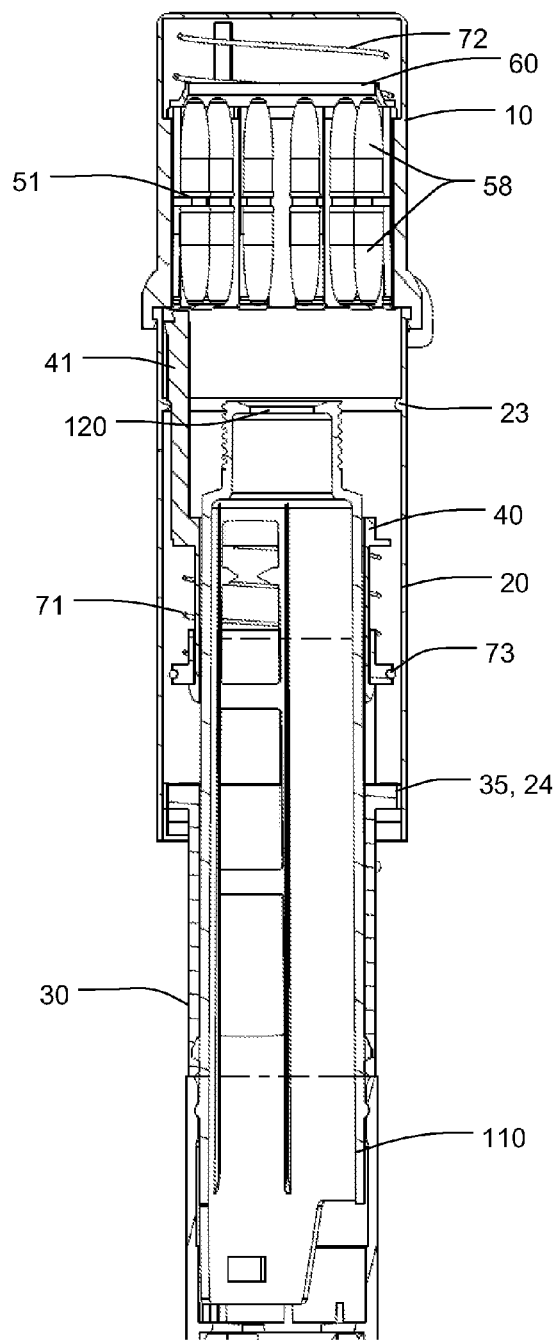
Figure 11B:
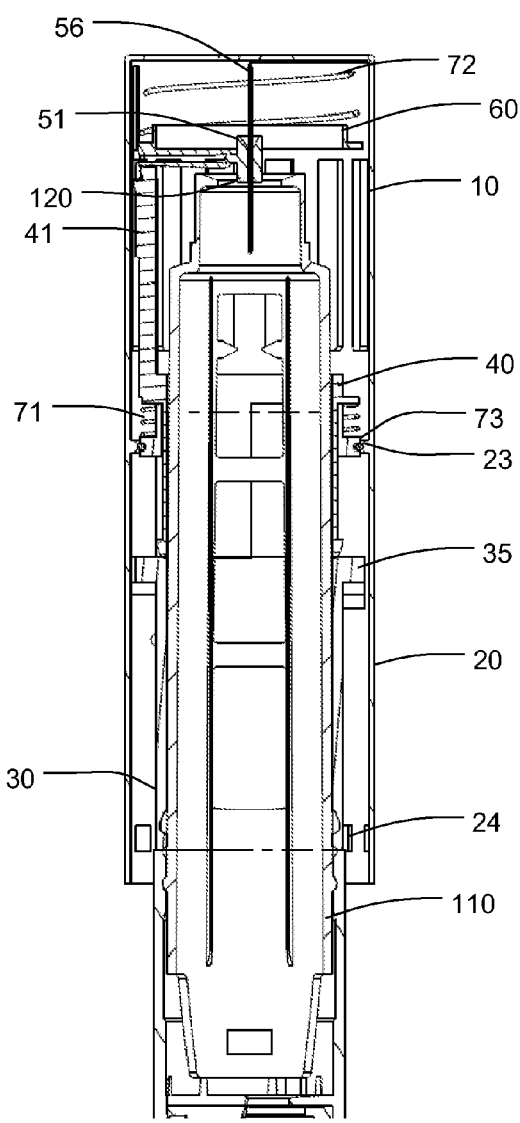
Figure 11C:
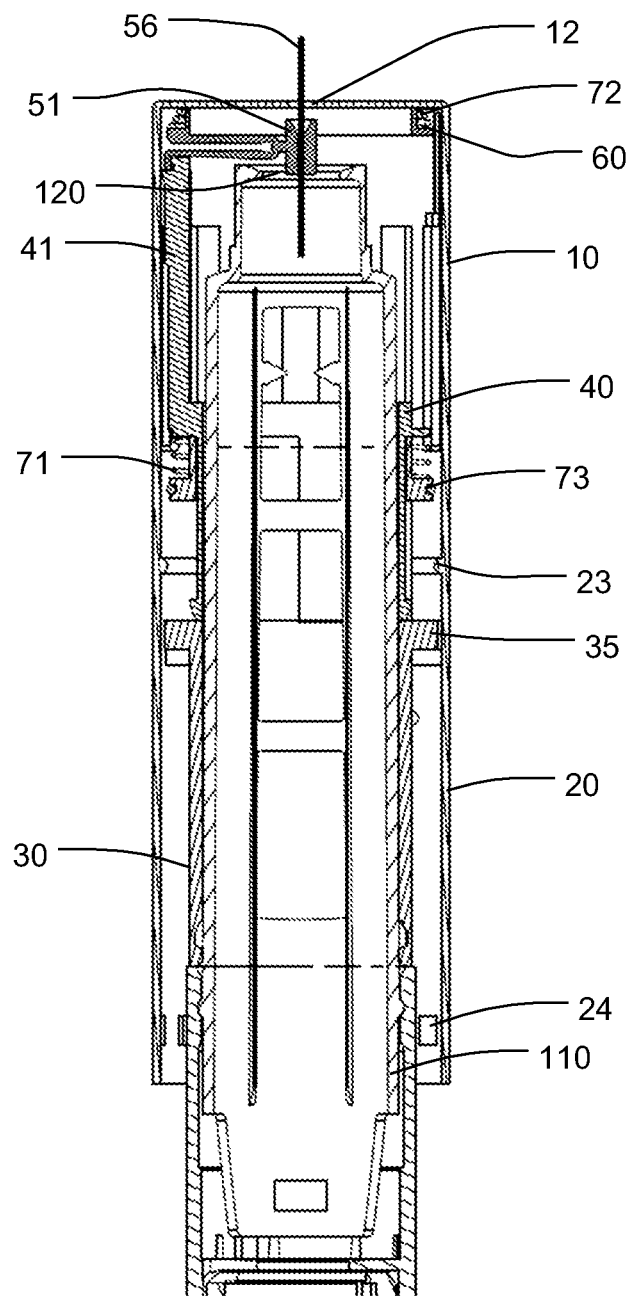
Figure 12:
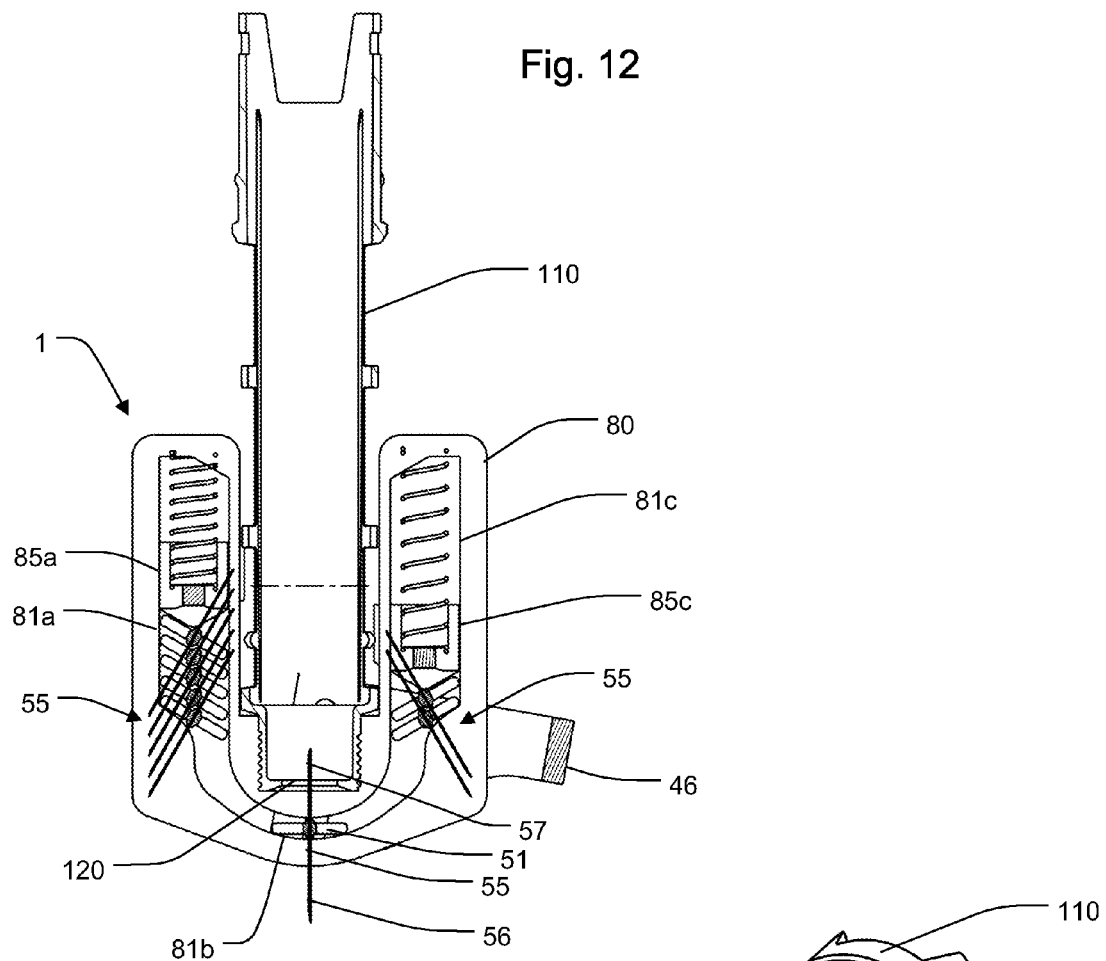
Figure 13:
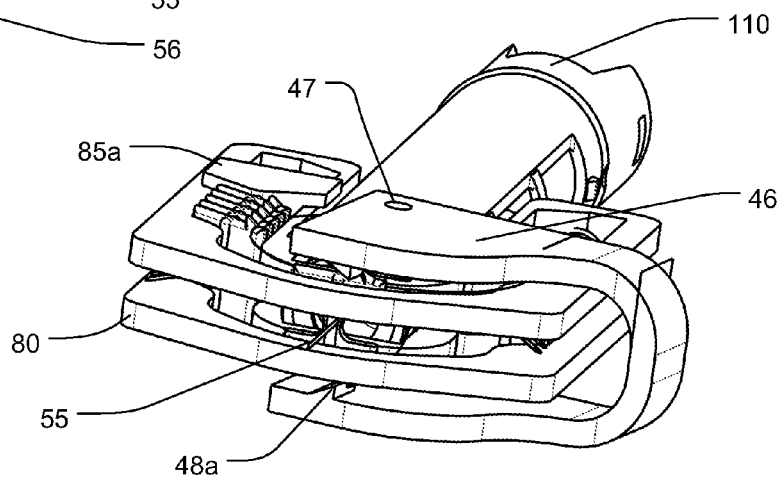
Figure 14:
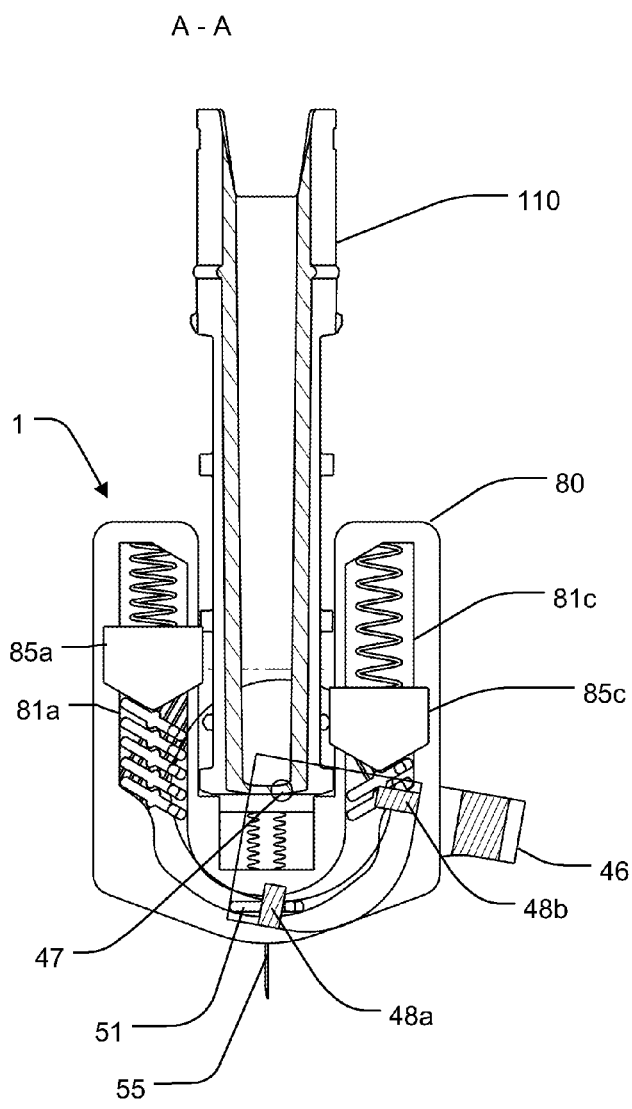
Figure 15:
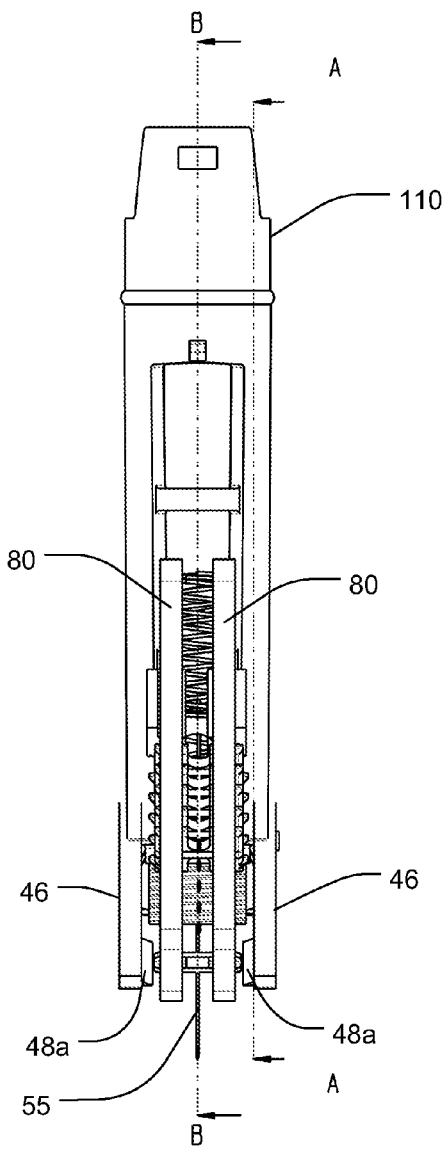

The invention will now be described in further detail with reference to the drawings in which:

FIG. 1 is a side view of an injection pen, a conventional cap and a needle magazine according to an embodiment of the invention, FIG. 2 is a perspective cross sectional view of the needle magazine shown in FIG. 1 mounted on an injection pen, FIGS. 3a and 3b show perspective and end views of a needle hub assembly of the needle magazine of FIG. 1, FIG. 3c is a perspective view of the needle hub assembly of FIGS. 3a and 3b, where sterility caps are mounted on the front and back needles of each injection needle, FIG. 4 is a perspective view of a needle hub assembly, an index member actuator arm and a needle mounting part of an injection pen, FIG. 5 is a perspective view of the index member shown of FIGS. 2 and 4, FIG. 6 is a perspective view of the needle hub assembly of FIGS. 3a and 3b, showing only a single needle being actuated into the needle mounting position, FIG. 7 is an end view of the proximal cap member of FIG. 2, FIG. 8 is a cross sectional side view of the proximal cap member shown in FIG. 2, FIG. 9 is a perspective view of the base member shown in FIG. 2, FIG. 10 is a perspective view of the needle magazine shown in FIG. 1, where the proximal cap member has been removed, FIGS. 11a, 11b and 11c are cross sectional side views of the needle magazine mounted on an injection pen. The figures show the assembly in a storage position, a septum penetration position and an injection position respectively, FIG. 12 show a needle magazine according to a second embodiment of the invention which is fastened to a cartridge holder of an injection device, FIG. 12 showing a cross sectional view through a needle array in a plane B-B intersecting the needles, FIG. 13 is a perspective front view of the needle magazine of the second embodiment, FIG. 14 is a cross sectional view of the needle magazine of the second embodiment in a plane A-A, and FIG. 15 is a side view of the needle magazine of the second embodiment.

FIG. 1 shows a prior art medical delivery device in the form of an injection pen 100 comprising a cartridge holder 110 for accommodating a medicament filled cartridge having a distal end closed by a piercable septum. The injection pen 100 comprises a needle mounting portion 120 arranged at the distal end of the injection pen. A needle mounting space is defined in the region distal to the needle mounting potion 120, i.e. the needle mounting space defines a cylindrical volume into which a needle may be introduced for subsequent coupling to the injection pen. A conventional injection needle (not shown) comprising a needle hub, a front needle and a back needle can be detachably mounted to the needle mounting portion 120 so that the back needle pierces the cartridge septum to thereby provide fluid communication with the cartridge interior. A conventional pen cap 200 is attachable to the injection pen 100 in order to protect the distal part of the pen, typically the cartridge holding part 110 as well as a conventional needle when mounted on the injection pen.

FIG. 1 also shows a needle magazine 1 according to a first embodiment of the present invention. The needle magazine 1 accommodates a plurality of injection needles which successively may be brought into an active position aligned with the septum part of the cartridge. The needle magazine 1 may be provided as a separate member intended to be removably attached to the injection pen 100 thereby substituting the conventional cap 200. Alternatively, the needle magazine 1 may be provided to be fixedly attachable to the injection pen 100 so that the pen and the needle magazine forms a disposable unit.

FIG. 2 shows a cross sectional view of the needle magazine 1 mounted onto the distal end of the injection pen 100 so that the longitudinal axis of the needle magazine is aligned with the pen device longitudinal axis. Needle magazine 1 includes a needle support structure which in the shown embodiment comprises a housing provided by distal cap member 10, proximal cap member 20 and base member 30. Base member 30 includes an opening adapted to receive the needle mounting portion 120 of the injection pen and means for attaching the needle magazine onto the injection pen e.g. by a snap connection. In some embodiments distal cap member 10 and proximal cap member 20 are rotationally fixed relative to each other. However, in the depicted embodiment, a lock out mechanism is incorporated allowing a user to rotate distal cap member 10 slightly with respect to proximal cap member 20 so as to enable a locked state where no needle can be moved away from the storage position.

Accommodated in distal cap member 10 is a needle hub assembly 50 which holds a series of injection needles. In the depicted state of the device, each needle is positioned in a storage position along the periphery of the distal cap member 2 so that all the needles are stored in a cylindrical array configuration. The needle magazine 1 includes a needle positioning mechanism for selectively moving a selected needle from its storage position into a needle mounting position substantially aligned with the needle mounting portion 120 of the injection pen. Base member 30 connects to index member 40 which carries an actuator member in the form of an actuator arm 41. In the depicted embodiment, the distal and proximal cap members 10, 20 along with needle hub assembly 50 may be rotated relative to base member 30 so as to align a selected needle with index actuator arm 41. By axially moving distal cap member 10 and proximal cap member 20 with respect to base member 30, the needle positioning mechanism is actuated by forcing index actuator arm 41 to move a selected needle into the needle mounting position. Continued axial movement of the cap members 10 and 20 with respect to base member 30 causes the selected needle to move axially with respect to the injection pen so that the back needle part of the selected needle penetrates the cartridge septum. By further moving cap members 10 and 20 with respect to base member 30, the front needle part of the selected needle protrudes through a needle passage, which in the depicted embodiment is provided as an opening 12 formed centrally in distal cap member 10. In an alternative embodiment, the needle passage 12 may be provided as a piercable septum.

FIG. 2 further depicts a first spring member 71, a second spring member 72 and a third spring member 73, the operative function thereof to be described later.

FIGS. 3a and 3b shows the needle hub assembly 50 of the first embodiment. The needle hub assembly comprises a distal ring 60 having two protrusions 59 extending radially outwards. Protrusions 59 are adapted to be received in corresponding axially extending grooves formed in an interior wall section of the distal cap member 10 (see FIG. 2) so that the hub assembly 50 is rotationally fixed but axially moveable with respect to distal cap member 10. The needle hub assembly 50 is biased in the proximal direction by second spring member 72 acting on distal ring 60.

Relative to distal ring 60 a plurality of injection needles 55, each mounted in respective hubs 51, are independently suspended in the proximal direction. In the depicted embodiment, 12 injection needles are accommodated in the needle magazine, each needle being a hollow double pointed cannula and forming a front needle for penetrating the skin of a subject user and a back needle for penetrating a cartridge septum. In the depicted state, the needle hub assembly holds each of the 12 needles in its respective storage position. Each hub 51 comprises a cylindrical part which holds the respective needle and a hub connecting member which extends radially outwards. From the hub connecting member distal beam 52 extends in the distal direction while proximal beam 53 extends in the proximal direction. For each needle, both distal beam 52 and proximal beam 53 are hingedly connected to the hub connecting member by a living hinge. Also distal beam 52 connects to distal ring 60 by a living hinge. The hinge sections may be provided as a film hinge.

As depicted in FIG. 3c, both the front needle section and back needle section of each particular needle 55 may be provided with sterility caps 58 made of a material such as silicone rubber. Sterility caps 58 are easily penetrated by the pointed ends of the front and back needle subject to forcing the front and back needle through needle opening 12 (see FIG. 2) and cartridge septum respectively.

Turning now to FIGS. 4-6, a needle position mechanism according to one embodiment of the invention will be described.

FIG. 4 shows a state of the needle magazine wherein the actuator arm 41 of the index member 40 has been rotationally aligned with a selected needle which is situated in its storage position. By axially moving the needle hub assembly 50 with respect to the index member, a distally directed force from the actuator arm 41 acts on the proximal end of proximal beam 53.

As best viewed in FIGS. 2 and 10, each beam sub-assembly 52/53, as defined by the particular needle positioned in its storage position, is confined in axially extending tracks formed in the internal wall of distal cap member 10 so that no part of beams 52 and 53 is allowed to move radially outwards and not allowed to move circumferentially. When a user applies a force to move the distal cap member 10 and hence the ring member 60 in the proximal direction the beams 52 and 53 are caused to move towards actuator arm 41. Due to the confinement of beams 52 an 53 by the inner surface of distal cap member 10, the part of the beams 52 and 53 which are connected to the needle hub 51 swivels radially inwards forcing the selected needle 55 into a central position within needle hub assembly 50. This is depicted in FIG. 6 (the remaining needles in their storage positions have been removed to improve clarity).

FIG. 5 is a perspective view of index member 40 having the actuator arm 41 extending in the distal direction. An endpoint surface of the actuator arm 41 is provided with a protrusion 42 adapted to snap into corresponding features at the proximal end of proximal beam 53. This snapping action cause the withdrawal of a needle into its storage position responsive to moving distal cap 10 and hence the needle hub assembly 50 away from the actuator arm 41.

Index member 40 is further provided with four axially extending legs 44 adapted to fit into corresponding axial recesses 34 of base member 30 (see FIG. 9) so as to make a splined connection allowing only axial movements between index member 40 and base member 30. Axial retaining members 45 in the form of protrusions serve to limit index member 40 in a maximum extracted position relative to base member 30. As seen in FIGS. 2 and 10, a first spring member 71 is situated between index member 40 and base member 30 so as to bias index member into its maximum extracted position relative to base member 30.

FIGS. 7 and 8 depicts an end view and a cross sectional view of the proximal cap member 20 while FIG. 9 depicts a perspective view of base member 30. The base member 30 shown in FIG. 9 forms a housing sleeve 31 forming a first opening which is adapted to encircle the distal end of the injection pen 100 and, in a situation of use, to retain the base member to the pen. When the needle magazine is in a state where all needles are kept in their storage position, the proximal cap member 20 may be rotated with respect to the base member 30 enabling the user to select a particular needle from the needle array by aligning the selected needle with respect to the actuator arm 41. In the depicted embodiment, an index mechanism urges proximal cap member 20 to rotate in discrete steps with respect to base member 30 to facilitate correct alignment. Also, in the depicted embodiment, base member 30 further comprise ratchet means cooperating with corresponding ratchet means of the proximal cap member 20 to ensure one way rotation. In this way, it is ensured that the index mechanism cannot rotate back to select and reuse a needle which has already been used.

When the needle magazine is in the state where the actuator arm 41 does not engage any of the needles, ratchet teeth 35 are axially aligned with ratchet teeth 24 formed in the interior of proximal cap member 20. A set of axial blocking members 36—half the number of ratchet teeth 35—are disposed along ratchet teeth 35 so as to align with every second ratchet tooth 35 and so that gaps are formed in between. In the depicted form, the ratchet teeth 24 corresponds in number to the number of axial blocking members 36. When the ratchet teeth 24 are rotationally aligned with the blocking members 36, the proximal cap member 20 is locked against axial movements with respect to the base member 30. In this situation, the needle magazine is in a proper storage state in between administrations where no needle is attached to the injection pen.

By rotating the proximal cap member 20 one step in the direction allowed, the teeth 24 aligns with the spacing between axial blocking members 36. In this state, the proximal cap member 20 is free to move axially with respect to base member 30 and the above described procedure of actuation of a selected needle into its needle mounting position is can be carried out. When axially returning the proximal cap member 20 into the state where no needle is engaged, further rotation of proximal cap member 20 with respect to base member 30 is possible. One step brings the needle magazine into the proper storage state. One further step brings the next consecutive needle into alignment with the actuator arm 41. This procedure may be repeated until each of the needles has been indexed and used. Additionally, the above indexing procedure may be limited to 360 degrees operation by a rotational lock provided by a protrusion 25 formed to protrude from the interior surface of proximal cap member 20. Protrusion 25 limits rotation by engaging rotation end stop 37 formed to protrude from the exterior surface of base member 30. A gap 26 allows the axial blocking members 36 to pass between ratchet teeth 24 and protrusion 25. A mounting groove 38 allow protrusion 25 to pass during assembly of the needle magazine. Proper design of the protrusion 25 retains proximal cap member 20 in an extreme extended position with respect to the base member 30.

The lock out feature addressed previously is provided by a lock out member 27 formed to protrude from the distal exterior surface of proximal cap member 20 and extending distally into a recessed region 16 of distal cap member 10. This lock out mechanism is in the depicted state designed to allow limited rotation, such as 10-15 degrees, between distal cap member 10 and proximal cap member 20. When use of a new needle magazine is initiated, the protrusion 25 is aligned with the gap between axial blocking elements 36 aligned with mounting groove 38. However, as the distal cap member 10 rotationally positioned in its lock out state, the needle hub assembly 50 is rotated out of alignment with the actuator arm 41 to prevent any actuation of the needles. Unlocking the lock out mechanism enables operation. When the last needle has been used and the cap members 20 have been moved to its extreme distal position, the lock out feature can be re-established by rotating the distal cap member 10 with respect to the proximal cap member 20. Subsequently, the used needle magazine may be safely discarded in a state where no needle is able to protrude through the needle opening 12.

As seen in the perspective view shown in FIG. 10 where the proximal cap member 20 has been removed to provide a better view, the needle magazine may be provided with indicia such as numbers or icons which may be aligned with an index pointer provided on a cooperating part of the device to indicate which needle is chosen or to provide indication that the device is in its proper storage state. Similar indications may be provided for the above described lock-out feature.

FIGS. 11a, 11b and 11c depicts three sectional views of the needle magazine when mounted on an injection pen and with the assembly in three different states during the operation of the needle magazine from a state wherein a needle has been indexed to an injection state. Due to clarity reasons, the cartridge including the piercable septum has been omitted from the drawings. It is to be noted that while FIG. 11a show the needle magazine holding the needles in their storage position and with sterility caps 58 covering the back and front needles, FIGS. 11b and 11c show the needle magazine without sterility caps and with only the selected needle visible, that is, the remaining non-selected needles has been omitted from the drawings in FIGS. 11b and 11c. Also, the lock-out feature is shown in FIG. 11a but has been omitted in FIGS. 11b and 11c.

FIG. 11a correspond to the condition where a particular needle has been rotationally aligned with respect to actuator arm 41 by rotating cap members 10 and 20 with respect to base member 30. Upon axially forcing cap members 10 and 20 towards the rear of the pen, the distal ring 60 of the needle hub assembly is initially moved relative to the actuator arm 41 so as to effect the selected needle to be positioned towards the centre of the assembly. Due to the geometry of the beam sections 52 and 53, the needle follows an arcuate path to end substantially in the centre above the cartridge septum. Due to a selected spring force of the first spring member 71 compared to the effective resistance against swivelling of the living hinge sections of the needle hub assembly 50, the first spring member 71 is not compressed in this initial phase of operation. Therefore, the index member 40 does not move during this initial phase. It is also to be noted, that since the spring constant of second spring member 72 is greater than the spring force of first spring member 71, no substantial movement occurs between distal cap member 10 and needle hub assembly 50 until relative movements between the index member 40 and the base member 30 has come to an end.

In the state shown in FIG. 11b the cap members 10 and 20 has been moved further towards the rear of the injection pen which causes the index member 40 to move towards the rear of the pen while compressing the first spring member 71. During this movement, the selected needle is moved in a substantially axial direction which causes the back needle to penetrate the seal of the cartridge and enter into the cartridge neck allowing fluid communication. In this state, the third spring member 73, being mounted on a flange at the distal end of base member 30, is aligned with an inner circular ridge 23 (see FIG. 2) protruding radially inwards from proximal cap member 20 (see FIG. 8). Spring member 73 and circular ridge 23 forms a detent mechanism so that the needle magazine keeps the state shown in FIG. 11b upon release of external forces.

In the state shown in FIG. 11c, the cap members 10 and 20 has been moved even further towards the rear of the pen while compressing second spring member 72. This procedure causes the front needle part 56 of the selected needle 55 to penetrate the sterility cap member 58 (not visible) and protrude through the needle opening 12 formed in distal cap member 10. This procedure is to be carried out, whenever the user wishes to perform an expelling action with the injection pen. Whenever an air shot operation is to be performed, cap members 10 and 20 may be manually gripped by a palm of the hand and forced into the state shown in FIG. 11c. In the event of performing an actual injection into tissue, the pen and needle magazine assembly may be pressed against the skin of the user, so as to effect the movements as sketched in FIGS. 11b and 11c. In that case, the needle is kept invisible during injection which is preferred by some users.

Whenever axial pressure is released from cap members 10 and 20, the needle magazine returns to the state as shown in FIG. 11b. Further withdrawal of cap members 10 and 20 releases the detent mechanism formed by members 23 and 73 and retracts the selected needle from the needle mounting position and into its storage position as depicted in FIG. 11a. As explained in relation with FIGS. 7-9 the needle magazine may further be operated by rotating the cap members 10 and 20 with respect to base member 30 one step to put the needle magazine into a storage position where cap members 10 and 20 are not able to move axially with respect to base member 30.

It is to be noted that other embodiments may comprise a needle hub assembly which is rotationally fixed with respect to the base member. In such an embodiment, the index member may be rotatably mounted relative to the base member, so that an actuator arm of the index member may be rotated so as to align with each particular needle in its storage position.

Within the context of the present invention, a needle magazine is also contemplated as a needle magazine having a needle hub assembly according to the above described embodiments but without the index mechanism for selectively choosing a particular needle. Such a needle magazine requires that the means for indexing, i.e. selecting a particular needle within the needle array, to be positioned completely or partly on the delivery device to which the needle magazine is intended to coorporate with. An embodiment could be provided as a medical delivery device having an actuator arm cooperating with the needle magazine, wherein the actuator arm is rotatably mounted on the delivery device. Alternatively, the actuator arm may be fixedly arranged on the delivery device, but wherein the needle hub assembly mounts rotatably with respect to the delivery device.

In a still further embodiment, the needle magazine is provided with a plurality of actuator members, each actuator member being dedicated a respective needle. Each actuator member is accessible from the exterior of the needle assembly and may be manipulated manually to cause a respective needle to move from its storage position to the needle mounting position. Each of the actuator members may be adapted to engage a proximal portion of the proximal beam in the same manner as explained in relation to FIGS. 4-6. Each of the actuator members may be formed to indicate whether the respective needle is in its storage position or in the needle mounting position, so that a user will readily notice whether attempting to choose a new needle will be obstructed by a previously selected and repositioned needle.

In the embodiment shown in FIGS. 1-11, the needle magazine is formed as a cylindrical member so as to adapt to a cylindrical injection pen. However, in other embodiments the overall design of the needle magazine may be differently shaped such as ovally shaped, box-shaped etc.

The needle hub assembly 50 is designed such that the needles when positioned in their storage position are aligned in a cylindrical configuration. However, other configurations are also possible within the context of the present invention, e.g. a cone shaped configuration, ovally shaped configuration etc. Such configurations may require amendments to the suspension mechanism which hold each needle, such as by forming the beam members differently. When the needle array is defined by a cone shaped configuration, the beam members may be designed to align the axis of the selected needle to be parallel with the axis of the injection device upon moving the needle from its storage position to its needle mounting position. In still alternative embodiments, a first sub-set of needles may be oriented in a first configuration and a second sub-set of needles arranged in a second configuration differing from the first configuration. Each particular needle of the first sub-set may be arranged so as to be meshed in between the needles of the second sub-set.

The needle hub assembly may be formed as a chain of interconnected needle support sub-assemblies which are able to articulate with respect to neighbouring needle support sub-assemblies. Such chain of sub-assemblies may be driven along a non-circular path during the index procedure so as to align a particular needle sub-assembly with the actuating mechanism before moving a selected needle into the needle mounting position. Such provisions ensure that a non-circular outer housing shape of the needle magazine correspond to the overall shape of the medical delivery device to which it is intended to be used. In such embodiment, a driving mechanism for driving the chain of needle support sub-assemblies along the non-circular path inside the needle magazine housing may be provided.

It is to be noted that the embodiment shown in FIGS. 1-11 is so designed that each needle after being moved into the needle mounting position subsequently penetrates the cartridge septum substantially at the same location. However, the lengths of the beams supporting the needles may be varied slightly from needle to needle so as to penetrate the septum at different locations at the needle mounting portion 120 of the device. In particular, when the needle hub assembly is mounted non-rotationally with respect to the cartridge, the needles may be arranged to pierce the septum of the cartridge a short distance offset from the centre of the cartridge, so that the array of needles penetrates the septum along a circle.

FIG. 12-15 show a needle magazine 1 according to a second embodiment of the present invention. The figures show the needle magazine 1 where the needle magazine has been mounted on a cartridge holder 110 associated with a medical delivery device (not shown). The cartridge holder 110 is configured for holding a medicament cartridge with a piercable septum schematically indicated as a fluid access portion 120.

The needle magazine 1 comprises a needle support structure 80 which as shown in FIG. 13 is provided as two base members arranged a small distance apart. Each of the base members define a segmented track 81a, 81b and 81c adapted to hold a series of injection needles 55, each supported by an independent needle hub 51, sandwiched therebetween so that the needles may be moved from new needle storage track 81a through a needle mounting position at track segment 81b and further to used needle storage track 81c. In the shown embodiment, a one-way mechanism is provided so that needles 55 may only be moved in the direction identified above along the segmented track. Such one-way mechanism may be provided by appropriately forming toothed surfaces (not shown) along the tracks 81a, 81b and 81c cooperating with protrusions formed on each respective needle hub 51. In the shown state, the needle magazine holds 5 new needles at new needle storage track 81a, one needle at the needle mounting position at track segment 81b and two used needles at used needle storage track 81c.

Base members 80 further forms an opening which is adapted to receive and/or to attach with the cartridge holder 110 so that the fluid access portion 120 of the medical delivery device is positioned in the vicinity of track segment 81b. When a selected needle 55 has been moved into a central location at track segment 81b, a back needle part 57 of the selected needle 55 is arranged pointing towards the fluid access portion 120 of the device. In this position, fluid communication with the selected needle 55 is performed by sliding the needle array with respect to the cartridge holder 110 of the medical delivery device.

A once mounted needle 5 may be disconnected from the fluid access portion 120 of the medical delivery device by sliding the needle magazine away from the device. Afterwards, the selected needle may be moved further to used needle storage track 81c.

In the shown embodiment an actuator member 46 is mounted rotatably with respect to base members 80 by means of rotating joint 47. In the depicted embodiment, actuator member 46 is moveable approximately 90 degrees from a forward position extending in the distal direction along the central axis of the cartridge holder 110 (position not shown in drawings) and into the position shown in FIGS. 12-14. In other embodiments, actuator member 46 is configured to move a shorter distance such as 72 or 60 degrees. Actuator member 46 is provided with protrusions 48a and 48b which is adapted to cooperate with protrusions formed on each of the needle hubs 51. When actuator member 46 is positioned in the forward position protrusions 48a engages the foremost needle 55 located in front at track 81a. At the same time, protrusions 48b engages the needle 55 located in the mounting position at track 81b. By turning actuator member 46 into the end position shown in FIGS. 12-14, the previous used needle located at the needle mounting position is moved to track 81c, while the foremost needle at track 81a is moved into the needle mounting position at track 81b, ready to be mounted on the medical delivery device. Subsequent sliding forward of the medical delivery device with respect to the needle magazine establishes fluid communication with the medicament reservoir of the medical delivery device.

A mechanism may be provided which in responsive to relative axial movements between needle magazine 1 and cartridge holder 110 turns actuator member 46, so that manual manipulation of actuator member 46 is avoided.

Spring actuated carriers 85a and 85b are respectively arranged in tracks 81a and 81c and configured to provide a biasing force on both new needles and used needles towards the front of the needle magazine. This ensures that the needles provided in track 81a and 81c are retained in their foremost positions so that they do not rattle. Furthermore, carrier 85 a ensures that actuator member 46 will always be able to engage a new needle 55 positioned at the front end of new needle track 81a as long as new needles remain at hand.

As readily apparent, an injection may be performed when a new needle 55 has been positioned at the needle mounting position and while the needle magazine 1 is attached to the medical delivery device. However, other embodiments may provide an attachment function of the selected needle and the medical delivery device, so that the selected needle may be separated from the needle magazine when the medical delivery device is removed from the needle magazine. In such an embodiment, the used needle track 81c may be omitted, acknowledging that used needles may be disposed of instead of being collected in the needle magazine.

Some preferred embodiments have been shown in the foregoing, but it should be stressed that the invention is not limited to these, but may be embodied in other ways within the subject matter defined in the following claims. The figures e.g. discloses medical delivery systems of the present invention in the form of an injection pen, however, this particular delivery device and its shape is in no way limiting for the present invention as defined in the claims.

The invention claimed is:

1. A needle magazine adapted for connection with a medical delivery device having a medicament reservoir and a device fluid access portion, the device fluid access portion, when the medical delivery device is coupled to the needle magazine, defining a needle mounting space in front of the device fluid access portion, the needle magazine comprising:
a needle support structure adapted to couple with the medical delivery device,
a plurality of injection needles supported by the needle support structure and forming a needle cluster, and
needle positioning element operable to move a needle selected from the plurality of needles from a storage position outside said needle mounting space and into a needle mounting position in said needle mounting space thereby allowing the selected needle to connect to the device fluid access portion to establish fluid communication with the medicament reservoir,
wherein the needle positioning element is configured to alter the relative position between a needle selected from said plurality of needles relative to a neighbour needle when said selected needle moves from its storage position to the needle mounting position,
wherein the plurality of needles when positioned in their storage position forms an array where the mutual spacing between a needle and a neighbouring needle is defined by a first distance,
wherein the needle positioning element, when moving a selected one of said needles from its storage position to the needle mounting position outside the needle mounting space and into the needle mounting position, moves said selected needle at least partly sideways relative to a respective neighboring needle so that the mutual distance between the needle in the needle in the needle mounting position to a neighbor needle is larger than said first distance, and
wherein each needle is mounted in a respective needle hub connected to a pivot support structure, said pivot support structure being configured to pivot the needle hub into the needle mounting position responsive to actuation of the positioning element.

2. A needle magazine as defined in claim 1, wherein the plurality of needles in their storage position are arranged in a ring-shaped array configuration and wherein, when the medical delivery device is coupled to the needle magazine, the needle mounting space is centrally located with respect to said plurality of needles in their storage position and wherein a needle selected from the plurality of needles is moved from a peripheral position into a central position upon moving the needle from its storage position and into the needle mounting position.

3. A needle magazine as defined in claim 1, wherein an actuator member is adapted to selectively engage at least one of the pivot support structures, said actuator member being moveably arranged with respect to the pivot support structure to actuate said pivoting movement.

4. A needle magazine as defined in claim 3, wherein the needle magazine comprises a cap member slideably arranged with respect to the medical delivery device when coupled thereto, said actuator member being adapted to actuate said pivoting movement responsive to sliding the cap member with respect to the delivery device.

5. A needle magazine as defined in claim 3, wherein the needle magazine further comprises a rotatable index mechanism for sequentially rotating and aligning said plurality of needles with respect to the actuator member.

6. A needle magazine as defined in claim 5, wherein the index mechanism is configured to operate in discrete steps and wherein the index mechanism further comprises means for axial blocking said slideable movement of the cap member at one or more pre-defined rotatable position(s) of the index mechanism.

7. A needle magazine as defined in claim 1, wherein the needle magazine comprises a cap member slideably arranged with respect to the medical delivery device when coupled thereto, wherein said sliding movement causes a front needle portion of a needle positioned in said needle mounting position to protrude through a needle passage formed in said cap member and/or causes a back needle portion of a needle positioned in said needle mounting position to penetrate the device fluid access portion of said medical delivery device.

8. A needle magazine as defined in claim 1, wherein the needle magazine needle magazine is adapted to removably attach to the a medical delivery device.

9. A needle magazine according to claim 1, wherein the the needle magazine attaches non-removably to the medical delivery device so as to form one unitary disposable assembly.

* * * * *